United States Patent
Gao

(10) Patent No.: US 9,993,562 B2
(45) Date of Patent: Jun. 12, 2018

(54) METALLIC GOLD CLUSTER MOLECULES AS THERAPEUTIC AGENTS FOR ARTHRITIC ANIMALS

(71) Applicant: Xueyun Gao, Beijing (CN)

(72) Inventor: Xueyun Gao, Beijing (CN)

(*) Notice: Subject to any disclaimer, the term of this patent is extended or adjusted under 35 U.S.C. 154(b) by 9 days.

(21) Appl. No.: 15/135,890

(22) Filed: Apr. 22, 2016

(65) Prior Publication Data

US 2017/0304408 A1 Oct. 26, 2017

(51) Int. Cl.
| | |
|---|---|
| *C01G 7/00* | (2006.01) |
| *A61K 47/48* | (2006.01) |
| *A61K 38/10* | (2006.01) |
| *A61K 38/06* | (2006.01) |
| *A61K 38/38* | (2006.01) |

(52) U.S. Cl.
CPC ........ *A61K 47/48015* (2013.01); *A61K 38/06* (2013.01); *A61K 38/10* (2013.01); *A61K 38/385* (2013.01)

(58) Field of Classification Search
None
See application file for complete search history.

(56) References Cited

U.S. PATENT DOCUMENTS

| | | |
|---|---|---|
| 8,383,919 B2 | 2/2013 | Gao |
| 9,090,660 B2 | 7/2015 | Gao |
| 2006/0172011 A1* | 8/2006 | Champion ............ A61K 39/35 424/489 |

OTHER PUBLICATIONS

Lee, Acsnano, vol. 8, No. 5, 4790-4798, 2014 (Year: 2014).*
Jie Zheng, et al, "Highly Fluorescent Noble-Metal Quantum Dots," Annu. Rev. Phys. Chem. 2007. 58:409-31 (Year: 2007).*
Jie Zheng, et al, "Highly Fluorescent Noble-Metal Quantum Dots," Annu. Rev. Phys. Chem. 2007. 58:409-31.

* cited by examiner

*Primary Examiner* — Satyanarayana R Gudibande
(74) *Attorney, Agent, or Firm* — Jie Tan; JT Law Office

(57) ABSTRACT

A therapeutic method for attenuating symptoms of inflammation and autoimmune diseases. This method includes preparing and administering to animals intraperitoneally or orally a metallic gold cluster complex preparation.

16 Claims, 14 Drawing Sheets

METALLIC GOLD CLUSTER MOLECULES AS THERAPEUTIC AGENTS FOR ARTHRITIC ANIMALS

CROSS-REFERENCE

Priority is claimed from the U.S. Provisional Patent Application No. 62/300,278, filed on Feb. 26, 2016, entitled "Au(0)-Peptide Molecules As Therapeutic Agent For Arthritis Animals," the entirety of which is hereby incorporated by reference for all purposes.

DESCRIPTION OF RELATED ART

The present application relates to metallic Au(0)-cluster-complex molecules, and more particularly to the use of metallic Au(0)-peptide cluster molecules as therapeutic agents for healing and suppressing the symptoms and development of arthritis in animals.

Note that the points discussed below may reflect the hindsight gained from the disclosed inventions, and are not necessarily admitted to be prior art.

Rheumatoid arthritis is characterized by persistent inflammation, pain, and joint swelling induced by autoimmune-mediated proliferation of synovial cells. Significant effort has been made by scientific and clinic community in finding cures for this disease. Patients of rheumatoid arthritis have failed to respond to many classic anti-inflammatory drugs and the different stages of this disease respond to treatment differently.

Aurotherapy that involves oral gold drug, Auranofin, both the injectable and the oral form, has remained the effective therapeutic method for rheumatoid arthritis, even though the problem of potential and sometimes significant toxicity remains largely unsolved.

The orally administered Auranofin form is a white odorless crystalline solid insoluble in water. The powder is unstable and must be protected from light and heat. A complex gold(I) chemical is the active gradient in Auranofin with a chemical name 2,3,4,6-tetra-o-acetyl-1-thio-β-D-glucopyranosato-S-(triethyl-phosphine)-gold in which the triethyl phosphine group stabilizes the gold(I) thiol complex (FIGS. 2A, 2B and 2C). There are many side effects with Auranofin. Diarrhea is the most commonly reported because the drug alters the absorption of salt and water by the colon and in the intestinal transport process. Other side effects include severe skin rash, proteinuria, eye problems, aplastic anemia and hematologic toxic reaction that are reportedly experienced in patients.

Since the gold(I) tends to degenerate into both metallic gold(0) atoms and oxidative gold(III) forms in vivo and in vivo metallic gold(0) atoms eventually form colloidal particles, it was postulated that the active ingredient in aurotherapy may be the colloidal metallic gold and the side-effects are caused by trivalent form gold(III). One report of oral administration of none-cationic colloidal gold to patients with long-standing erosive rheumatoid arthritis has been shown to have improved the swelling and joint tenderness in patients by G. Abraham, et al, in *Journal of Nutritional & Environmental Medicine* (1997) 7: 4, 295-305. But it remains a myth as to the effect since there is no subsequent report or any other scientific or clinic studies to verify this reported effect. At the same time, there have been many other reports of colloidal gold being ineffective. It is not clear whether the reported effect of colloidal gold is reliable or whether there is a difference in effectiveness between the amount of colloidal gold and the status of colloidal gold, in treatment of rheumatoid arthritis.

Rheumatoid arthritis remains to be the most common autoimmune disease that is associated with progressive disability, systematic complications, and early death. Current disease-modifying therapies only produce limited or partial responses. Reliable predictive therapeutic responses and toxicity are lacking. Because synovial inflammation tends to perpetuate, sustained remission is almost impossible to achieve for autoimmune diseases and requires ongoing pharmacologic therapy, there is always a great need in the development of non-toxic therapeutic agents for the treatment of rheumatoid arthritis and other auto-immune related inflammatory diseases.

SUMMARY

The present application discloses a method of administering gold(0) cluster complex molecules in treatment of or preventing rheumatoid arthritis and auto-immune inflammation.

Stable metallic gold cluster molecules are obtained. In one embodiment, sufficient amount liquid suspension of metallic gold cluster is intraperitoneally administered to animals having rheumatoid arthritis or autoimmune inflammation to mitigate the development and progression of the disease.

In one embodiment, sufficient amount liquid suspension of metallic gold cluster complex molecules is orally administered to animals having rheumatoid arthritis or autoimmune inflammation.

BRIEF DESCRIPTION OF THE DRAWINGS

The disclosed application will be described with reference to the accompanying drawings, which show important sample embodiments of the invention and which are incorporated in the specification hereof by reference, wherein.

DETAILED DESCRIPTION OF SAMPLE EMBODIMENTS

Figure 1A:
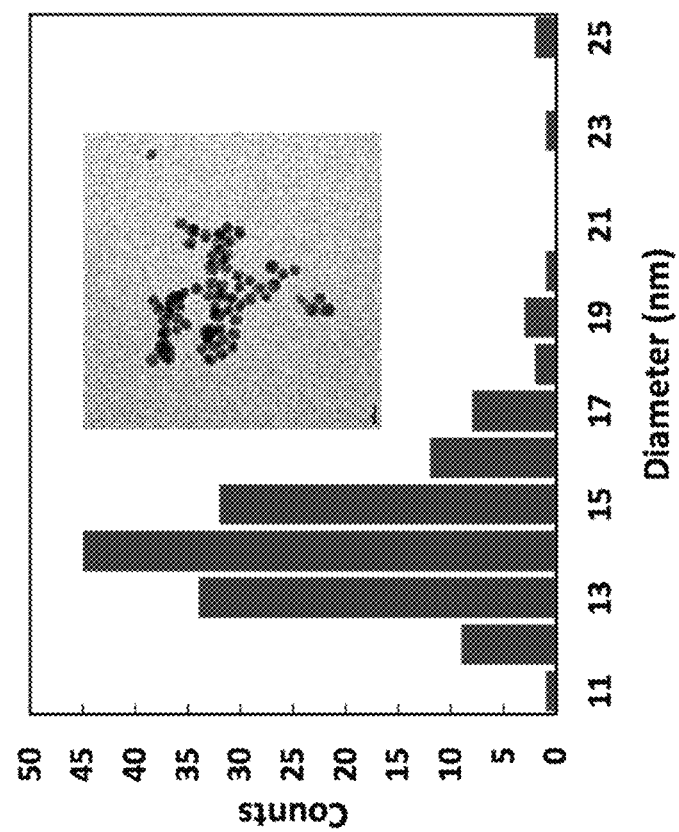
FIG. 1A is an illustration in bar graph of size distribution showing size heterogeneity of gold colloidal preparation in prior art.

The numerous innovative teachings of the present application will be described with particular reference to presently preferred embodiments (by way of example, and not of limitation). The present application describes several embodiments, and none of the statements below should be taken as limiting the claims generally.

For simplicity and clarity of illustration, the drawing figures illustrate the general manner of construction, and description and details of well-known features and techniques may be omitted to avoid unnecessarily obscuring the invention. Additionally, elements in the drawing figures are not necessarily drawn to scale, some areas or elements may be expanded to help improve understanding of embodiments of the invention.

The terms "first," "second," "third," "fourth," and the like in the description and the claims, if any, may be used for distinguishing between similar elements and not necessarily for describing a particular sequential or chronological order. It is to be understood that the terms so used are interchangeable. Furthermore, the terms "comprise," "include," "have," and any variations thereof, are intended to cover non-exclusive inclusions, such that a process, method, article, apparatus, or composition that comprises a list of elements is not necessarily limited to those elements, but may include other elements not expressly listed or inherent to such process, method, article, apparatus, or composition.

The term "autoimmune disease" refers to the category of diseases in animals where there is the presence of self-reactive immune response e.g., auto-antibodies that cause self-attacking and self-destruction by macrophage cells.

The term "metallic gold cluster" refers to the gold-atom cluster complex molecules wherein the gold atoms form a geometric crystal structure. The gold geometric crystal structure is often stabilized by polymeric capping molecules through forming non-covalent metal bonds with thiol or selenol or phosphine or amine or arginine side group contained in the polymeric molecules. These polymeric molecules can be peptides containing a thiol or arginine or selenol or phosphine or amine side groups. Metallic gold cluster molecules usually emit fluorescent emissions under UV excitations. Gold-cluster molecules are generally prepared in mild reductive reaction conditions at room temperature with the presence of polymeric capping molecules in the reaction.

The term "metallic gold-peptide cluster complex" or "metallic gold(0)$_n$-peptide$_m$" or "metallic peptide$_m$-gold$_n$" or "metallic Au$_n$-peptide$_m$" or "peptide$_m$-Au$_n$" molecule are used inter-exchangeably, these are metallic gold cluster complex molecules that are stabilized by forming metal bonds with a thiol or selenol or phosphine or amine or arginine side group containing peptides or polypeptides, where the n and m respectively represents the number of gold atoms and peptide molecules in the complex.

The term "gold cluster capping molecule" refers to a thiol or selenol or phosphine or amine or arginine side group containing peptide or polymeric molecule that can form non-covalent metal bonds with gold atoms, thus stabilizing a gold-cluster geometric structure. These molecules include lipids, poly-lysine, poly-arginine, poly-asparagine, poly-aspartic acid sodium salt, poly-aspartic acid sodium salt, poly-glutamate, PEG (poly ethylene glycol), PLGA (poly (lactic-co-glycolic acid)), protein, polysaccharides, nucleic acid, and their degraded products, bio-polymeric molecules of digestion extracts from various biological sources, including plants, animals, bacteria and fungi, and the standard forms are readily available from a commercial source Metallic gold cluster molecules are structurally different to the traditional gold colloidal particles which are not fluorogenic.

The term "colloidal metallic gold" refers to the high density metal gold particles that are formed by densely packed gold atoms. They are sphere gold particles in a variety of sizes (FIG. 1). The colloidal gold particles have no geometric surface other than being round and the number of gold atoms are not predictable. In a typical colloidal gold preparation the sizes of generated gold particles are heterogeneous in a wide range; this type of gold particles has no fluorescent emission. The most common colloidal gold preparation method is by reacting trisodium citrate, as the reducing agent, in aqueous solution with tetra-chloroaurate dehydrate at an elevated heated temperature close to a boiling or refluxing temperature. See Frens, G., "controlled nucleation for regulation of particle size in monodisperse gold suspensions," *Nature Phys. Sci.* 1973, 241: 20-22, the entirety of this article is incorporated by reference.

The term "rheumatoid arthritis" refers to the disease that is generally characterized by synovial inflammation and hyperplasia ("swelling"), autoantibody production, cartilage and bone destruction ("deformity"). Rheumatoid arthritis in patients is the result of complex interplay among genotype and environmental triggers. It often has high levels of cellular and humoral immune responses to type II collagen. Polyarthritis can be induced in rats and mice by intradermal injection of type II collagen emulsified in Freunds adjuvant. Various animal models have been established based on type II collagen induced inflammation. Some inbred strains of mice, such as MRL/lpr, are known to develop with age an autoimmune disease that resembles human systemic lupus erythematous, and these mice also are reported to spontaneously develop arthritis and have humoral responses to type I and type II collagen. It is reported that the susceptibility of mice to arthritis and immune responses to collagen are under the control of the major histocompatibility complex (MHC) genes and certain particular epitopes of the human leukocyte antigen locus confer particular susceptibility. That is probably because that predisposing T-cell repertoire selection, antigen presentation or alteration in peptide affinity has a role in promoting auto-reactive adaptive immune responses.

One of the autoimmune problems is stemmed from impairment of the macrophage-mediated phagocytic process. For example, cytokines, such as those secreted by adipocytes, collectively named as adipokines, are reported to be involved in the activation of macrophage cells. Studies of adipose tissues in obese individuals and in animal models indicate that adipose tissues are infiltrated by a large number of macrophages and this recruitment is linked to systemic inflammation. The presence of macrophages is to remove apoptotic cells in an immunologically silent manner to prevent the release of noxious substances. Macrophage cells can be activated to express different phenotypes by different cytokines, and macrophage cells of different phenotypes in turn lead either to more production of pro-inflammatory cytokines and cascades of inflammation or the more production of anti-inflammatory cytokines and resolution of inflammation. The recruitment and activation of macrophages are influenced by T cells of different surface cluster differentiation proteins and cytokines. Different activations of macrophages thus generate either a pathogenic and inflammatory environment or a non-inflammatory and protective environment. M2-like phenotype macrophages are related to the non-inflammatory and protective healing.

Many of the cytokines and epitope proteins are cysteine-rich. For example, adipokine resistin is a member of the cysteine-rich family of resistin-like molecules that are associated with the activation of inflammatory processes. Transcription of resistin gene is induced by pro-inflammatory cytokines including IL-1, IL-6 and TNF. It is also reported that resistin directly counters the anti-inflammatory effects of adiponectin on vascular endothial cells by promoting the expression of the pro-inflammatory adhesion molecule 1, intercellular adhesion molecule 1 and pentraxin 3 in these cells, enhancing leukocyte adhesion. Adiponectin on the other hand can bind to apoptotic cells and facilitate their uptake by macrophages. Phagocytosis of early apoptotic cells in turn promotes an M2-like phenotype in macrophages which remove apoptotic cells in an immunologically silent manner, protecting the organism from systematic inflammation.

Figure 2C:
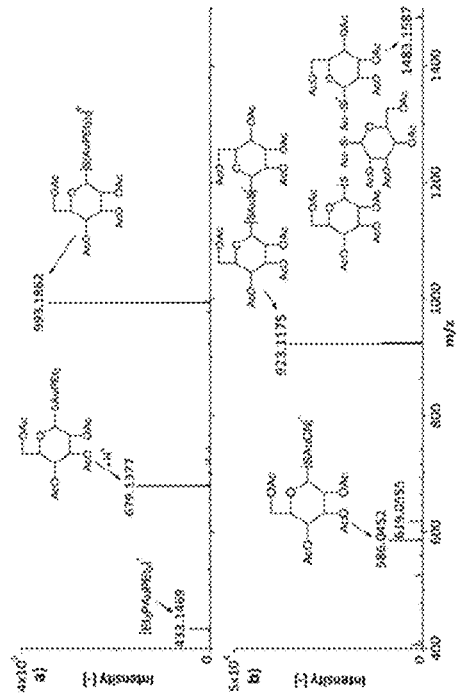
FIG. 2C is the mass spectrometry of the gold compound, the active ingredient of Auranofin.
Figure 2B:
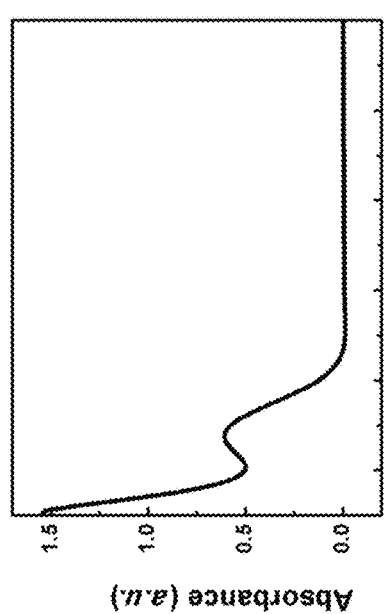
FIG. 2B is the absorbance spectrum of the gold compound, the active ingredient of Auranofin.
Figure 2A:
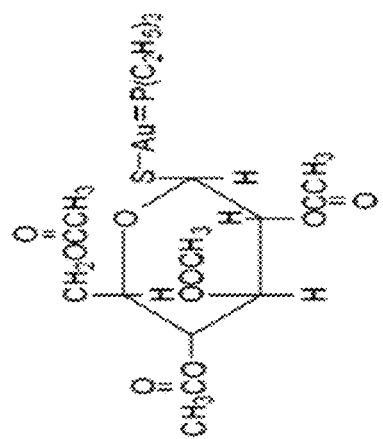
FIG. 2A is the chemical structure of the gold compound, the active ingredient of Auranofin.
Figure 3:
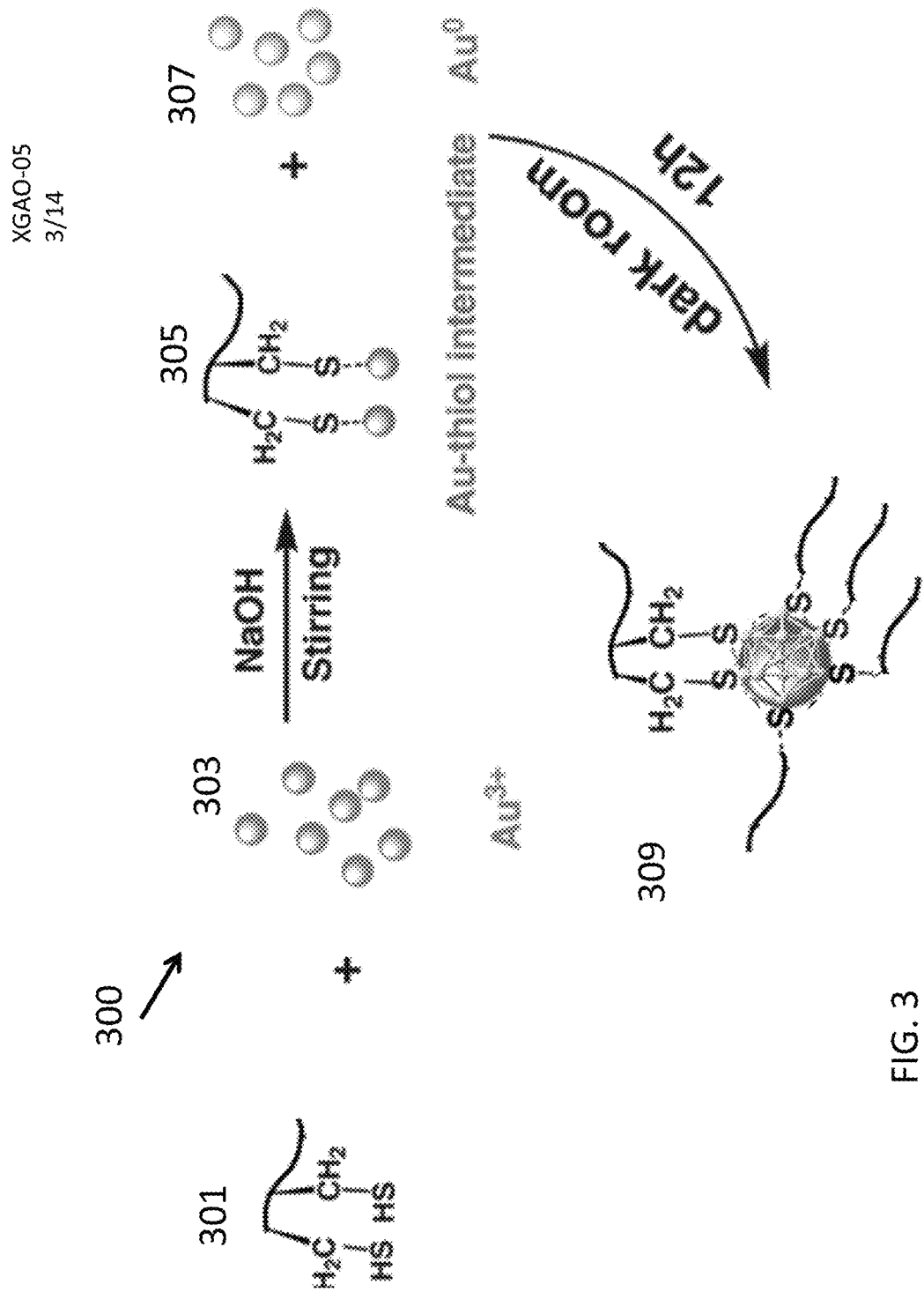
FIG. 3 figuratively illustrates an example reaction process of generating a metallic gold(0)-peptide cluster molecule.
Figure 3B:
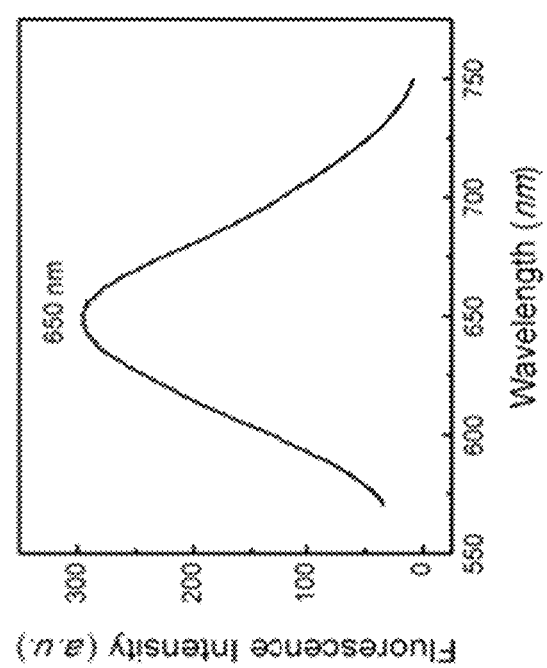
FIG. 3B is the fluorescence spectrum of the metallic peptide$_9$-gold$_{25}$ complex molecule of FIG. 3A in accordance with this application.
Figure 3A:
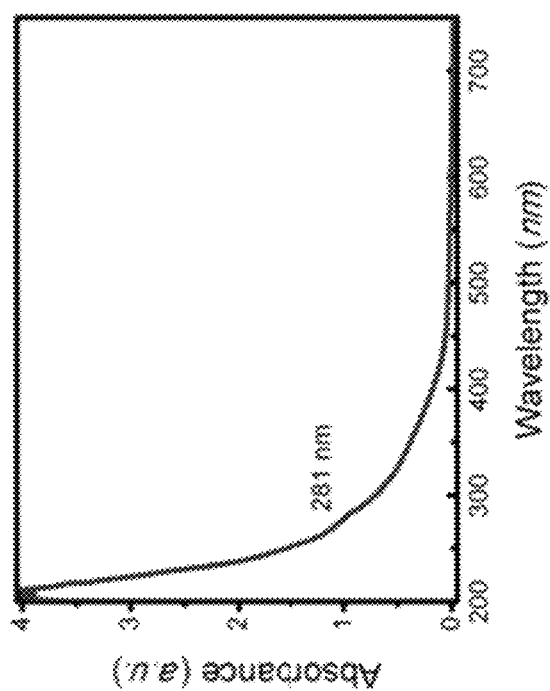
FIG. 3A is the absorbance spectrum the metallic peptide$_9$-gold$_{25}$ complex molecule using peptide of SEQ ID NO: 1 in accordance with this application.
Figure 3C:
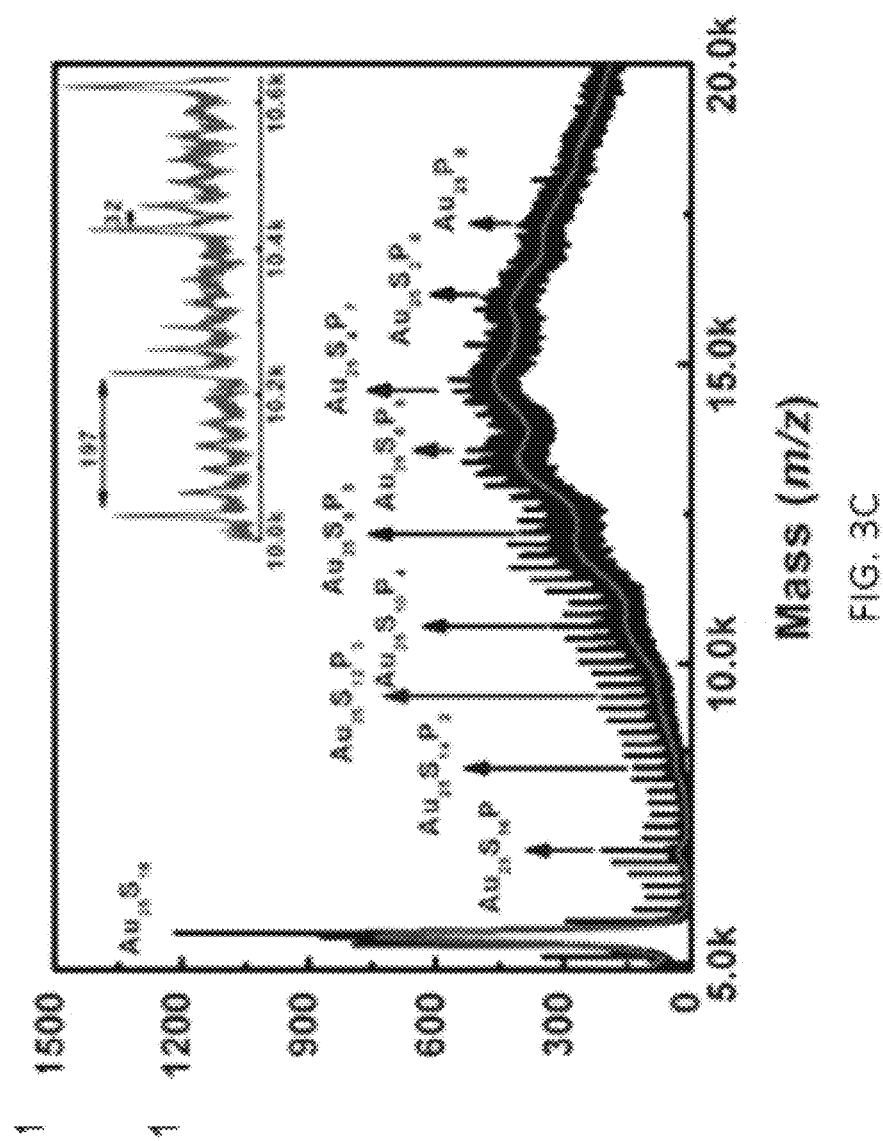
FIG. 3C is the mass spectrometry of the metallic peptide$_9$-gold$_{25}$ complex molecule of FIG. 3A in accordance with this application.

As shown in FIGS. 1A-5, different to colloidal metallic gold (FIG. 1A) which is densely packed solid gold particle under electronic microscope and of variety of sizes, the peptide-gold cluster complex molecules are stable and of gold atom clusters of well-defined molecular formula, size and geometric structure (FIGS. 3A, 3B and 3C). Their physical appearance and properties are different in that they have different UV-light absorbent spectra and mass spectrometry. Their structural differences are evidenced by their absorption spectra shown in FIG. 3A and the existence of fluorescent emission (FIG. 3B). The mass spectrometry shows precise molecular formula. For example, in FIG. 3C 25 Au atoms form a cluster which binds 9 peptides.

Gold cluster molecules are also different to gold salt. In another comparison, the gold chemical 2,3,4,6-tetra-o-acetyl-1-thio-β-D-glucopyranosato-S-(triethyl-phosphine)-gold in Auranofin is shown in FIGS. 2A, 2B and 2C, and the gold atom is in oxidized status and cannot form metallic bonds.

Gold cluster complex molecules possess metallic surface that can form none covalent, but stable metallic bonds with thiol chemical groups. Typical preparation reaction is illustrated in FIG. 3. Also see U.S. Pat. No. 8,383,919 to Gao, X, the entirety of which is incorporated by reference. Gold-cluster complex are stabilized by thiol or selenol or phosphine or amine or arginine side group containing polymeric molecules, collectively called gold cluster capping molecules which may be peptides containing a thiol or arginine or selenol or phosphine or amine side groups. As shown by the example in FIG. 3C, in which the gold-peptide cluster molecule preparation is made of homogenous gold crystal-like clusters with a fixed number of gold atoms where each gold-cluster molecule binds finite number of thiol-containing cysteine rich peptides non-covalently. However, these non-covalent metal bonds formed between peptides and gold crystal atoms will allow the competitive bindings of other cysteine rich proteins or peptides in vivo, making gold-cluster complex a good non-toxic, non-intrusive therapeutic candidate molecules for regulating the level of cysteine rich proteins in vivo.

Although inflammation is involved in causing rheumatoid arthritis, many classic anti-inflammatory drugs are not effective in preventing or in treatment of rheumatoid arthritis even though they may suppress the level of antibody production or the immune-related acute inflammatory responses. For detailed testing results, see K. Phadke et al. *Immunopharmacology*, entitled "Evaluation of the Effects of Various Anti-Arthritic Drugs on Type II Collagen-Induced Mouse Arthritis Model," 1985, vol 10, page 51-60, entirety of this article is incorporated by reference.

Gold-peptide nano-cluster molecules have been shown to cause apoptosis in vitro. See U.S. Pat. No. 9,090,660 to Gao, X, the entirety of which is incorporated by reference. Gold-peptide cluster molecules bind cysteine-rich peptides in vitro (FIG. 3C). Cysteine-rich cytokines are associated with the generation of pro-inflammation environment in vivo, as shown in the example of resistin and resistin-like cytokines. Binding of cysteine-rich cytokines by gold-clusters will reduce the amount of these cytokines to cause inflammation. Apoptosis in turn induces the activation of anti-inflammation macrophages. Having these two anti-inflammation associated properties, can gold-peptide-cluster molecules be a good candidate for anti-inflammation and for treatment rheumatoid arthritis in vivo? The experiments herein on animal model in this application show that metallic gold cluster molecules administered intraperitoneally demonstrate significant anti-inflammation effect as well as anti-rheumatic effect. Oral administering of metallic gold cluster molecules also showed some effect albeit not as effective as administering intraperitoneally.

The positive results of metallic gold clusters in both anti-inflammation and anti-rheumatic effects in animal model indicate a great potential for metallic gold cluster molecules as a new category of therapeutic agent for rheumatoid arthritis. Another attractive aspect of metallic gold cluster molecules is their nature of having no apparent toxicity in vivo. Due to the perpetual nature of rheumatoid arthritis being an auto-immune disease where symptoms returns once treatment stops, non-toxicity is certainly as important as effectiveness, if not more.

Preparation of Metallic Gold-Peptide Cluster Molecules

In preparing stable nano-sized metallic gold clusters using peptides containing a tyrosine or cysteine residues, the peptides also function as the stabilizing agent for the crystal like structure of the metallic gold cluster. Other binding polymeric molecules can also be used as stabilizing agents, these molecules include lipids, poly-lysine, poly-arginine, poly-asparagine, poly-aspartic acid sodium salt, poly-aspartic acid sodium salt, poly-glutamate, PEG, PLGA, proteins, polysaccharides, nucleic acids, and their degraded products, bio-polymeric molecules of digestion extracts from various biological sources, including plants, animals, bacteria and fungi, and the standard forms are readily available from a commercial source.

Example 1

For clarifying reasons, the example in this application is conducted using a published peptide sequence (SEQ ID NO: 1) Cys-Cys-Tyr-Gly-Gly-Pro-Lys-Lys-Lys-Arg-Lys-Pro-Gly. See Liu, R., et al, "The Au Clusters Induce Tumor Cell Apoptosis via Specifically Targeting Thioredoxin Reductase 1 (TrxR1) and Suppressing Its Activity", *Chem. Commun.*, 2014, 50, 10687-10690. The chemical reaction is as the following:

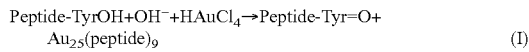

$$\text{Peptide-TyrOH} + \text{OH}^- + \text{HAuCl}_4 \rightarrow \text{Peptide-Tyr=O} + \text{Au}_{25}(\text{peptide})_9 \quad (I)$$

All chemicals were purchased from Sigma-Aldrich, unless otherwise indicated. Ultrapure water was used throughout the experiments. The peptides with 95% purity were chemically synthesized by a solid phase method (China Peptides Co. Ltd.). All glassware were washed with aqua regia, and then rinsed with ultrapure water and ethanol. An aqueous solution of $HAuCl_4$ (25 mM, 80 µL) was slowly added to peptide solution (1.06 mM, 1880 µL) in a 5 mL vial under vigorous stirring at room temperature, then NaOH (0.5 M, 40 µL) was added within 30 seconds to give a final pH of ~10. The sample was sealed and stored in the dark for 15 hours without any disturbance to produce the products. The generated products were dialyzed for 12 hrs (Dialysis Tube MWCO=500) to remove free $HAuCl_4$ and NaOH, and the sample was further concentrated by ultrafiltration tube (Millipore, MWCO: 3000) to remove free peptides. The obtained metallic gold(0)-peptide cluster molecules are suspended in the water and kept in dark at 4° C. for further testing. Structures are tested through UV-spectrum and fluorescent spectrums, and mass spectrometry.

FIGS. 3A and 3B shows the absorbance and fluorescence emission peak are located at 281 nm and 650 nm, respectively. The mass spectrometry (FIG. 3C) result indicates the obtained gold complex is a 25 gold atom cluster having maximum of 9 binding peptide molecules, i.e. $Au_{25}$(peptide)$_9$.

Example 2

A metallic gold-peptide cluster complex sample is made using peptide (SEQ ID NO: 2) Glu-Cys-Gly (GSH) following a published procedure similar to the procedure in EXAMPLE 1 with the chemical reaction (II). See Luo, Z., et al, "From Aggregation-Induced Emission of Au(I)-Thiolate Complexes to Ultra bright Au(0)@Au(I)-Thiolate Core-Shell Clusters", *J. Am. Chem. Soc.*, 2012, 134, 16662-16670.

$$\text{GSH} + \text{OH}^- + \text{HAuCl}_4 \rightarrow \text{Au}_{25}(\text{SG})_{18} + \text{GS-SG} \quad (II)$$

Figure 4C:
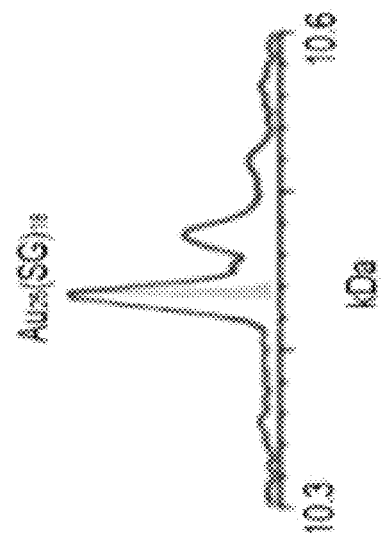
FIG. 4C is the mass spectrometry of the metallic peptide$_{18}$-gold$_{25}$ complex molecule of FIG. 4A in accordance with this application.
Figure 4B:
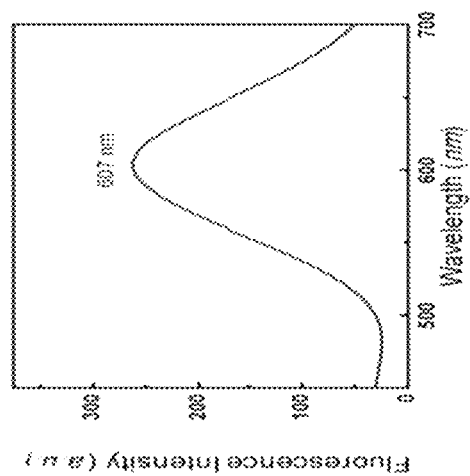
FIG. 4B is the fluorescence spectrum of the metallic peptide$_{18}$-gold$_{25}$ complex molecule of FIG. 4A in accordance with this application.
Figure 4A:
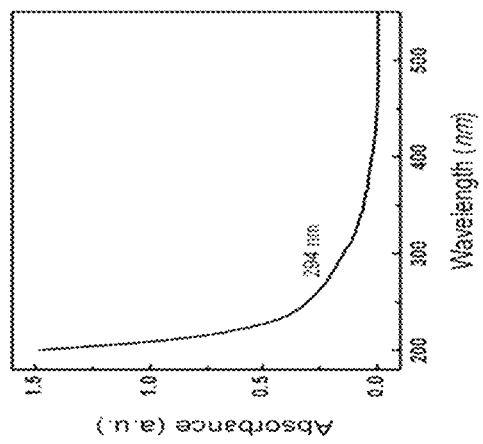
FIG. 4A is the absorbance spectrum the metallic peptide$_{18}$-gold$_{25}$ complex molecule using peptide of SEQ ID NO: 2 in accordance with this application.
Figure 5:
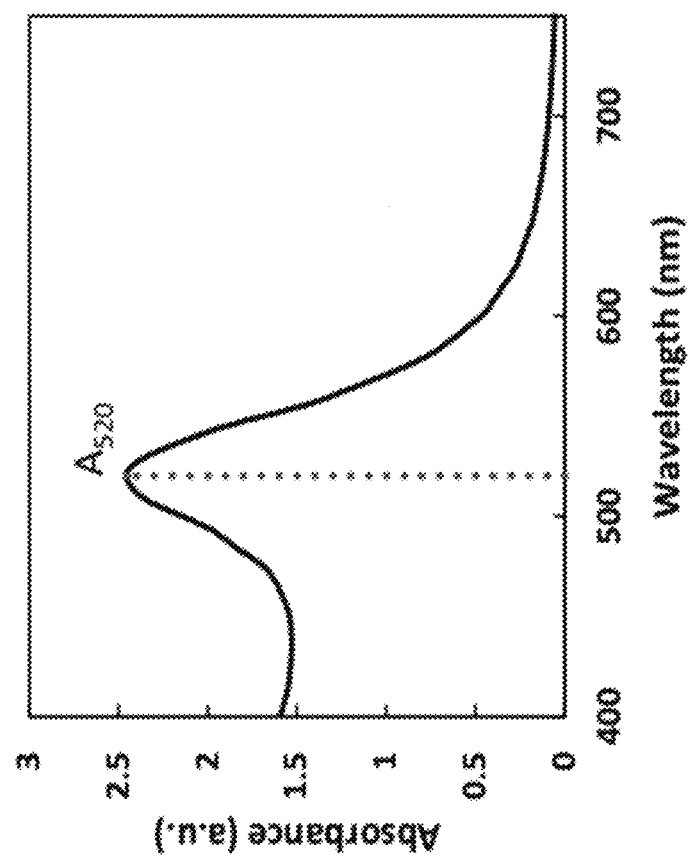
FIG. 5 is the absorbance spectrum the metallic HAS-gold$_{4000}$ complex molecule in accordance with this application.

FIG. 4C is the mass spectrometry of the generated gold-peptide cluster molecule having a molecule formula of $Au_{25}(SG)_{18}$. FIGS. 4A and 4B show the absorbance and fluorescence emission spectra of the gold $Au_{25}(SG)_{18}$ cluster molecule. The absorbance and the maximum fluorescence emission peak are located at 294 nm and 607 nm, respectively.

Example 3

A metallic gold-peptide cluster complex sample is made using human serum album protein (HSA) with the following chemical reaction:

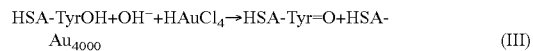

$$\text{HSA-TyrOH} + \text{OH}^- + \text{HAuCl}_4 \rightarrow \text{HSA-Tyr=O} + \text{HSA-Au}_{4000} \quad (III)$$

All chemicals were purchased from Sigma-Aldrich, unless otherwise indicated. Ultrapure water was used throughout the experiments. All glassware were washed with aqua regia, and then rinsed with ultrapure water and ethanol. Aqueous $HAuCl_4$ solution (5 mL, 10 mM, 37° C.) was added to HAS solution (5 mL, 5 mg/mL, 37° C.) under vigorous stirring. Two minutes later, NaOH solution (0.5 mL, 1 M) was introduced and the reaction was allowed to proceed under vigorous stirring at 37° C. for 12 hours. After the reaction, the sample was concentrated by a dialysis tube (MWCO: 100 kDa) to remove un-reacted free HSA, NaOH and $HAuCl_4$. The obtained HSA-bound AuCs are suspended in the water and kept in dark at 4° C. UV-VIS spectrum (FIG. 5) of HSA-bound metallic gold cluster molecules shows the characteristic absorbance peak at around 520 nm, resulting from characteristic local surface plasmon resonance (SPR).

Animal Experiment

Collagen induced arthritis in mice has been the standard animal model for studying rheumatoid arthritis and other polyarthritis. DBA/1 male mice weighted 20-22 grams were purchased from Hua-Fu-Kang Biotechnology Limited, Beijing, China. Type II collagen and Complete Freund's Adjuvant were purchased from Chondrex Inc., Redmond, Wash., USA. Auranofin was purchased from Sigma, USA and Dexamethasone was purchased from Jin-Yao Amino Acid Company, Tianjing, China. $Gold_{25}$(peptide)$_9$ cluster molecules were prepared according to Example 1.

Type II collagen was dissolved in 0.1 mM acetic acid solution and was emulsified with equal volume of Complete Freund's Adjuvant to make a 1.0 mg/ml Type II collagen emulsion. After one week of resting and environment adjustment, DBA/1 male mice were divided into groups, each group was consisted of 10 mice. Each animal was injected intradermally at the 2-3 cm base of the tail an emulsion of 100 µg Type II collagen. On day 21, a second booster dose of 100 µg Type II collagen emulsion was injected. Negative control group of mice are injected with equal amount of 0.9% Sodium Chloride solution.

On day 22, groups of mice were given different drugs once each day for 28 days (4 weeks) until day 49 (end of week 7). The groups of mice were examined for inflammation and status. Group 1 (normal group) and negative control group (nondrug-treated control group) mice received intragastrically 0.9% Sodium Chloride solution; Group 2 mice received oral administration of 0.5 mg/kg body weight Dexamethasone (Dex); Group 3 mice received oral administration of 1 mg/kg body weight Auranofin; Group 4 mice received oral administration (i.g.) of 50 mg/kg body weight $gold_{25}$(peptide)$_9$ cluster solution; Group 5 mice received intraperitoneally (i.p.) 5 mg/kg body weight $gold_{25}$(peptide)$_9$ cluster solution.

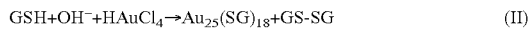

TABLE 1

The Effect of Treatment on Mice Body Weight (g) (mean ± sd)

| Group | 0 w | 1 wk | 2 wk | 3 wk | 4 wk | 5 wk | 6 wk | 7 wk |
|---|---|---|---|---|---|---|---|---|
| Normal Group (0.9% N.S) | 21.65 ± 1.16 | 23.12 ± 0.84 | 23.72 ± 1.18 | 24.25 ± 1.30 | 24.33 ± 0.87 | 24.83 ± 0.82 | 25.28 ± 0.95 | 25.22 ± 0.64 |
| Nondrug-treated Control group (0.9% N.S) | 20.95 ± 1.32 | 22.65 ± 1.53 | 23.00 ± 1.89 | 23.45 ± 1.52 | 21.75 ± 1.37## | 21.88 ± 1.55## | 22.30 ± 1.01## | 22.10 ± 1.56## |
| DEX (i.g. 0.5 mg/kg) | 21.20 ± 1.14 | 22.70 ± 1.09 | 23.20 ± 1.06 | 23.50 ± 1.02 | 21.60 ± 1.90 | 21.06 ± 1.46 | 21.66 ± 1.28 | 22.19 ± 1.13 |
| Auranofin (i.g. 1 mg/kg) | 21.60 ± 1.17 | 23.25 ± 1.11 | 23.75 ± 1.11 | 24.35 ± 1.53 | 22.10 ± 1.10 | 21.74 ± 1.14 | 23.24 ± 0.08* | 23.33 ± 0.25* |
| $Au_{25}$(peptide)$_9$ (i.g. 50 mg/kg) | 21.60 ± 1.31 | 23.05 ± 1.04 | 23.40 ± 1.33 | 24.10 ± 1.50 | 22.66 ± 1.64 | 22.35 ± 1.73 | 23.23 ± 1.71 | 23.43 ± 1.47* |
| $Au_{25}$(peptide)$_9$ (i.p. 5 mg/kg) | 22 ± 1.27 | 23.25 ± 1.21 | 24.13 ± 0.99 | 24.00 ± 0.85 | 23.30 ± 0.84** | 23.01 ± 0.70* | 22.63 ± 1.71 | 22.47 ± 1.43 |

$p < 0.01$ vs. the normal group;
*$p < 0.05$;
**$p < 0.01$ vs. the non-drug-treated group.

Comparing to the none-treated mice group, intradermal injection of type II collagen immunization induced weight loss in all groups after 1 week of the second booster collagen injection (week 4). Anti-inflammation drug dexamethasone did not reverse the body weight loss, while all the gold agents treated mice groups had slight body weight recovery.

Figure 6:
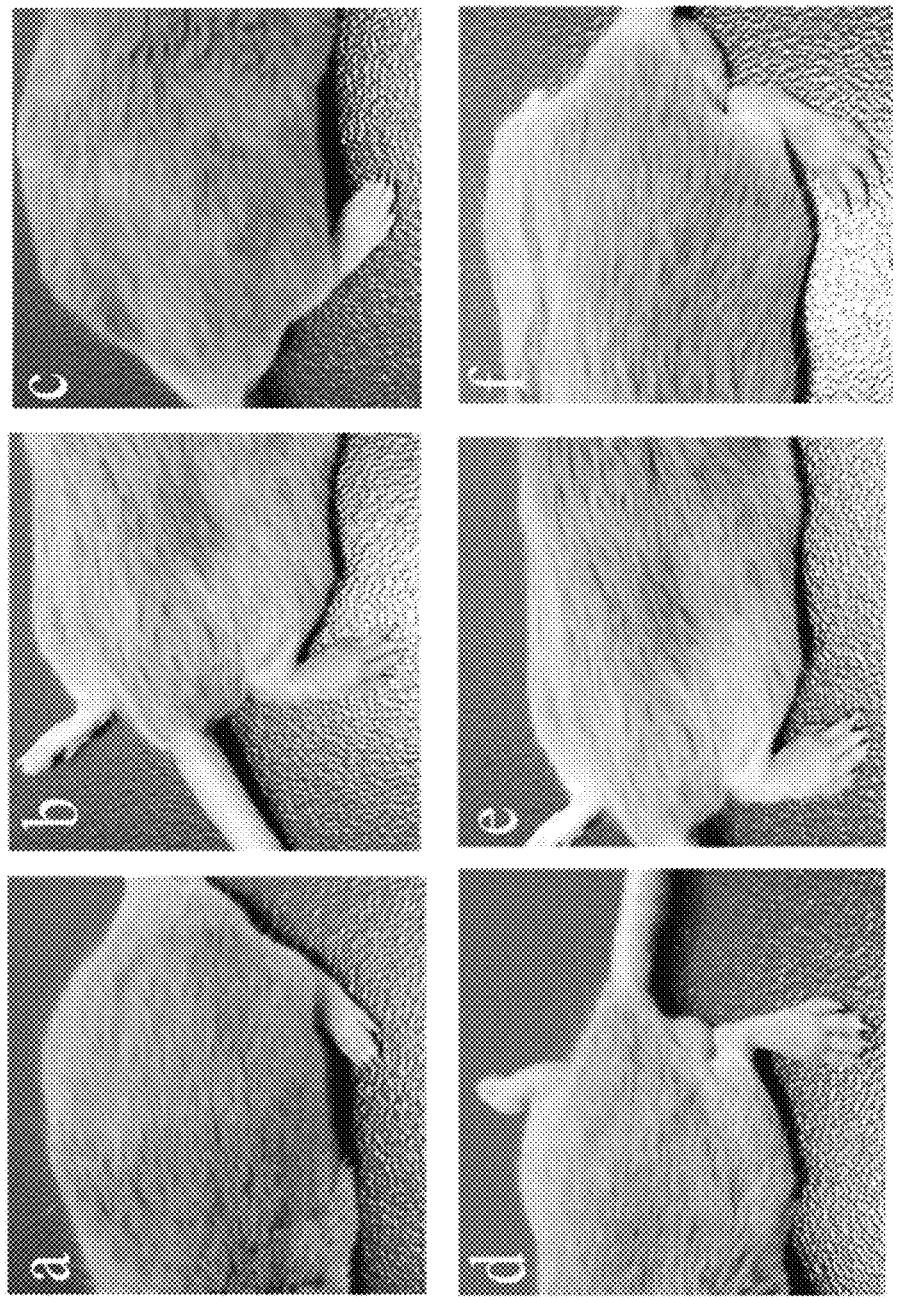
FIG. 6 shows the photo pictures of the hind limbs of the mice of different experiment groups in accordance with this application.

FIG. 6 shows the pictures of swelling their hind limbs of each animal group at the end of 7 weeks of the experiment. Swelling starts to become visible around 4 weeks, one after the second collagen injection, it generally peaks at the week 5-6, two to three weeks after the second injection of collagen. In FIG. 6, a shows the paw of normal mouse, no swelling; b shows the none drug treated immunized mouse where type II collagen induced swelling and deformation around the toes, paw and ankle; c shows Dex treated mouse with no obvious swelling; d shows Auranofin treated mouse with swelling and no obvious improvement; e shows the gold$_{25}$(peptide)$_9$ cluster molecule orally administered mouse with still obvious swelling and slightly better condition; f shows the gold$_{25}$(peptide)$_9$ cluster molecule i. p. administered mouse with obvious reduced swelling and improvement in deformation.

The inflammation was assessed by means of a visual scoring method where mouse individual paws were graded from 0-4 as follows:

0 score: no redness and no swelling;

1 score: mild erythema at the toes;

2 scores: toe joints and paw swelling;

3 scores: swelling below ankle 4 scores: all ankle and paw swelling.

All four limbs of each mouse were examined and scored, and scores of all four limbs were added together for each mouse.

The evaluation results of all groups are shown in Table 2.

TABLE 2

The effects of anti-inflammation drug treatment

| Group | 35 d | 38 d | 42 d | 45 d | 49 d |
|---|---|---|---|---|---|
| Normal (0.9% N.S) | 0.00 ± 0.00 | 0.00 ± 0.00 | 0.00 ± 0.00 | 0.00 ± 0.00 | 0.00 ± 0.00 |
| None drug treated Inflamed group (0.9% N.S) | 7.13 ± 4.05## | 7.63 ± 3.16## | 8.15 ± 3.48## | 9.85 ± 2.96## | 10.33 ± 3.08## |
| DEX (i.g. 0.5 mg/kg) | 0.22 ± 0.44** | 0.33 ± 0.71** | 1.22 ± 1.30** | 1.33 ± 1.00** | 1.22 ± 0.97** |
| Auranofin (i.g. 1 mg/kg) | 6.66 ± 2.00 | 5.77 ± 3.42 | 8.11 ± 2.47 | 8.33 ± 3.42 | 9.88 ± 3.06 |
| $Au_{25}$(peptide)$_9$ (i.g. 50 mg/kg) | 6.13 ± 3.09 | 7.00 ± 3.07 | 8.88 ± 3.04 | 8.88 ± 3.52 | 9.13 ± 0.48 |
| $Au_{25}$(peptide)$_9$ (i.p. 5 mg/kg) | 8.00 ± 2.78 | 7.77 ± 4.49 | 7.00 ± 3.20 | 6.38 ± 2.33* | 5.88 ± 3.40* |

$p < 0.01$ vs. the normal group;
*$p < 0.05$,
**$p < 0.01$ vs.the non-drug-treated group.

Type II collagen induced significant inflammation and gross deformity at the paws and limbs of the mice in the non-treated group throughout 5 week to 7 week period of experiment. The swelling and inflammation is immediately suppressed in the mice group received oral administration 0.5 mg/kg body weight dexamethasone in the second week of treatment; mice received oral administration 1 mg/kg body weight Auranofin had slightly lower swelling scores; and mice received oral administration 50 mg/kg body weight gold$_{25}$(peptide)$_9$ cluster solution, showed better scores than Auranofin, but still developed comparable inflammation by the end of 4 weeks of treatment; the swelling and joint deformity was significantly improved in mice received intraperitoneally 5 mg/kg body weight gold$_{25}$(peptide)$_9$ cluster solution at the 3' week of treatment, and the improvements become significantly better as the treatment of time of treatment increases.

Figure 7:
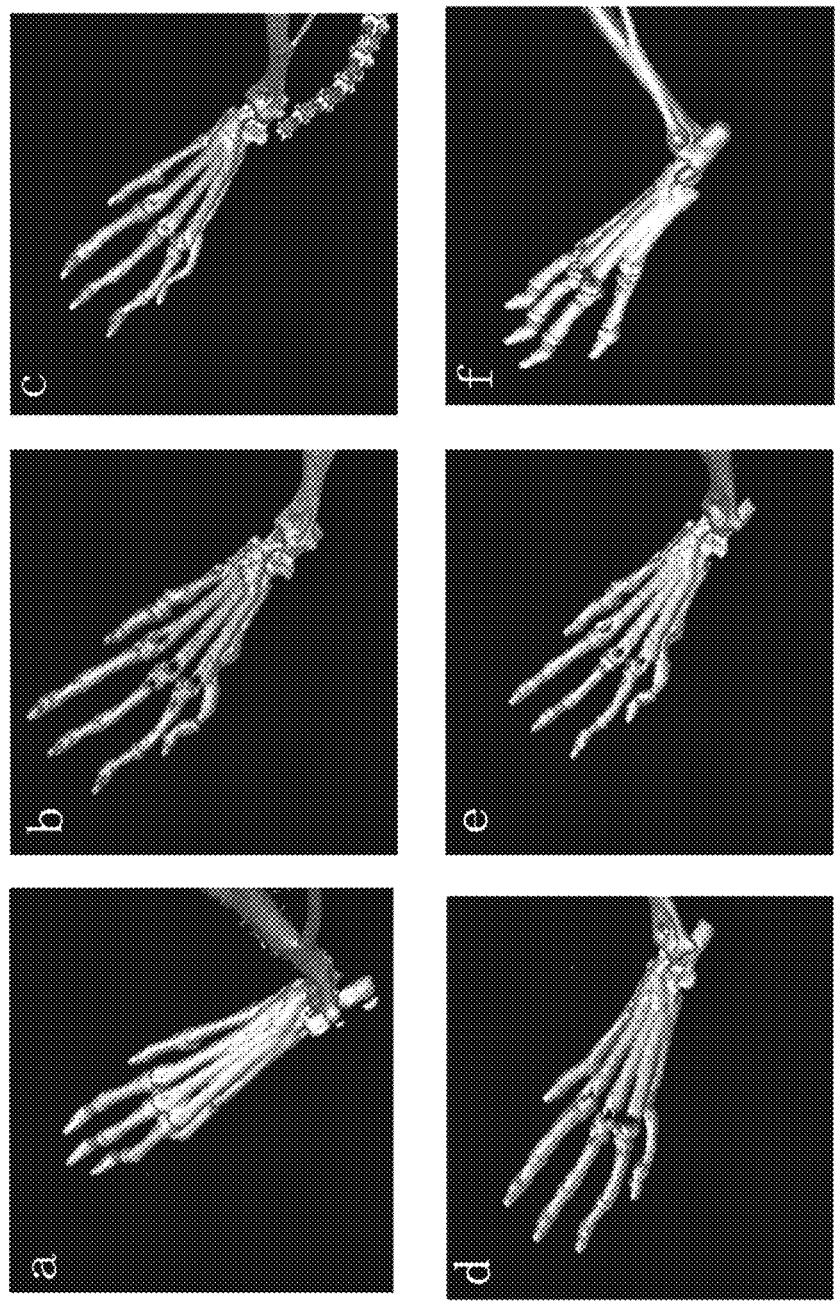
FIG. 7 shows the radiographs of the hind limbs of the mice of different experiment groups in accordance with this application.

In reference to FIG. 7, the therapeutic effect is illustrated with the pictures of 3D CT scan images of mice of individual groups, showing the bone density changes of paw joints at the end of 7 weeks of drug treatment. Picture a shows the paw of a normal mouse, no osteolysis; b shows the none drug treated immunized mouse where type II collagen induced arthritis caused obvious bone deformation and osteolysis at the digital joints; c shows that Dex treatment prevented bone deformation and no obvious osteolysis at the end of week 7; d shows the Auranofin treated mouse and e shows the gold$_{25}$peptide$_9$ cluster molecule orally administered mouse, both mouse groups still developed bone deformation and osteolysis at the end of week 7; f shows the gold$_{25}$(peptide)$_9$ cluster molecule i.p. administered mouse, there is significant improvement on the bone density comparing the non-treated arthritis mice, and no obvious osteolysis and only slight bone deformation. Intraperitoneally administering gold-peptide-cluster molecules thus demonstrates significant effectiveness in anti-inflammation as well as anti-rheumatic effect. Especially at the longer time period of administration.

Figure 8:
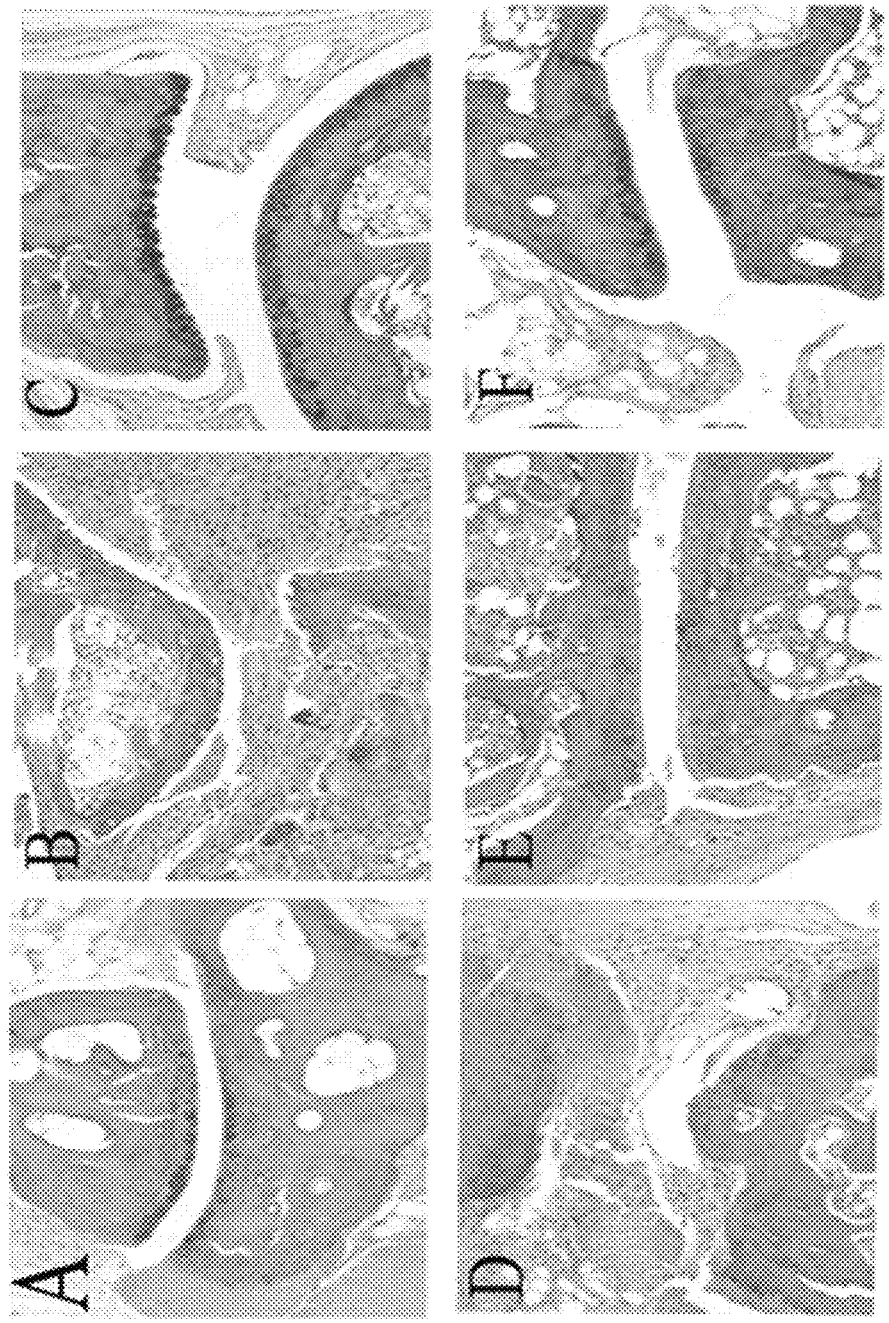
FIG. 8 shows the histologic staining of the hind limb joint sections of the mice of different experiment groups in accordance with this application.

To evaluate the soft tissue damages around the joint area, the joint tissues of the hind limbs of each mouse groups were then fixed, embedded, sectioned into slides and hematoxylin and eosin stained to examine the histology and histopathology changes at the joints. FIG. 8 shows the staining results of the various mice groups. A is the picture of the normal joint area with no invasion of synovial macrophages; B is the picture of type II collagen induced arthritic joints without any treatment, where there are significant bone erosion and soft tissue damages, infiltration of large number of synovial macrophage cells; C is the picture of joints of Dex treated mice, no significant bone erosion and no obvious synovial macrophage invasion; D shows the pictures of the joints of mice treated with Auranofin, there are significant soft tissue damages at the joint areas, and large number of infiltration of synovial macrophage cells; E and F are the pictures of the joint area of mice treated with gold$_{25}$(peptide)$_9$ cluster molecules, through orally or i.p. administering method respectively, the bone erosion is significantly less and no apparent number of synovial macrophage cells infiltration in F; orally administering gold-peptide-cluster in E shows reduced soft tissue damages and less macrophage infiltration. Both orally and intraperitoneally administering gold-peptide-cluster molecules thus demonstrates significant anti-inflammation as well as anti-rheumatic effect, however, intraperitoneally administering gold$_{25}$(peptide)$_9$ cluster molecules is much more effective method.

Figure 9:
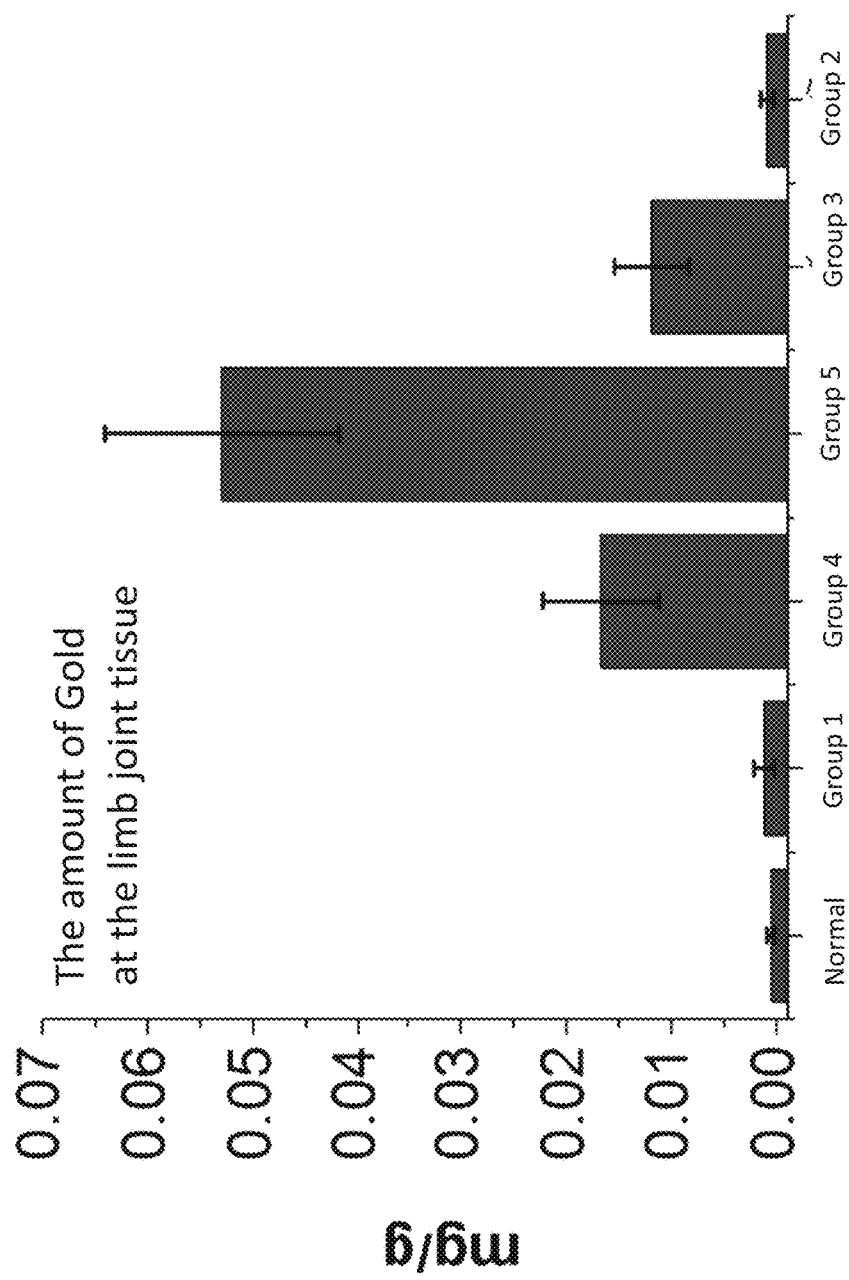
FIG. 9 graphically shows the amount of gold at the limb joint area of the different experiment groups of FIG. 6.

In reference to FIG. 9, the amount of gold was measured at the arthritic joints of the variously treated mice groups. It shows that intraperitoneally (group 5) administering of gold agents allows significantly higher amount of gold being transported to the arthritic joints than the orally administering method (group 4), presumably through the phagocytosis uptake of activated macrophage cells. Less but comparable amount gold is also observed for auranofin treatment (group 3).

Figure 10:
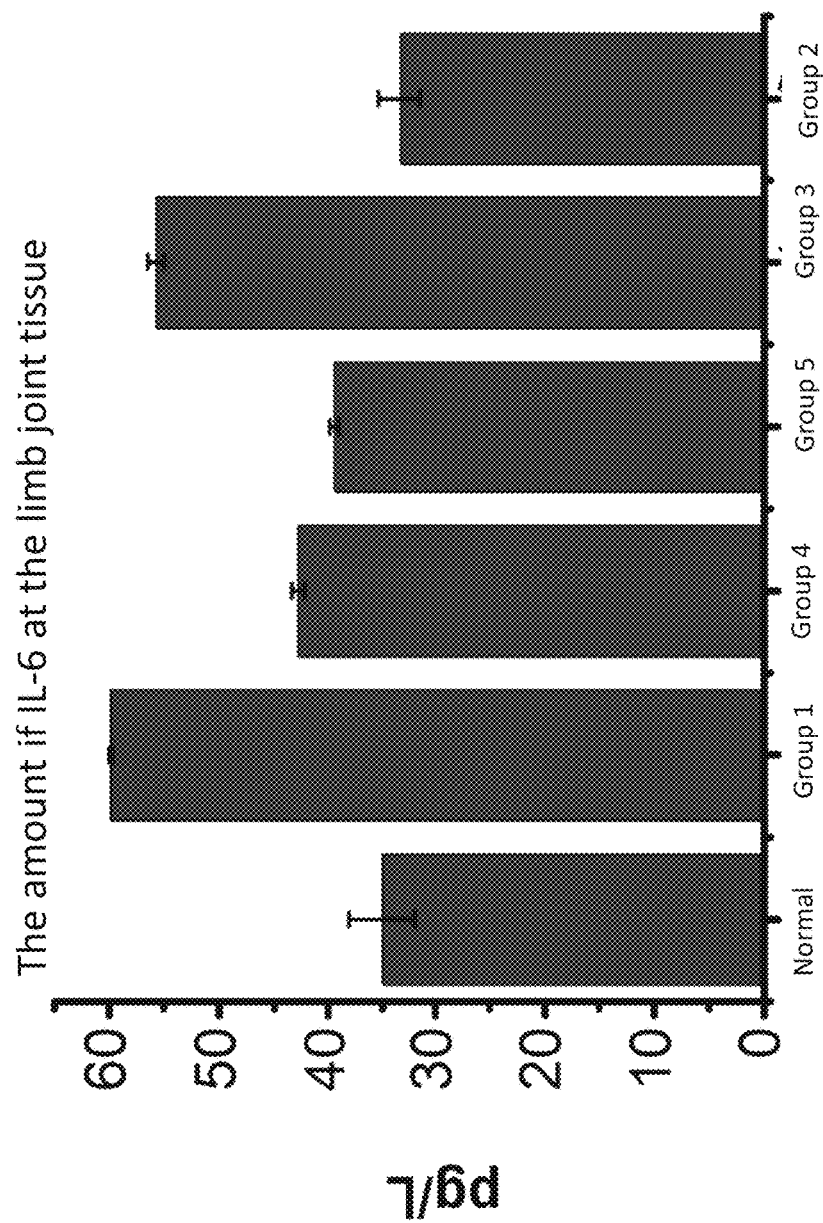
FIG. 10 graphically shows the amount of inflammatory cytokine IL-6 factor at the limb joint area of the different experiment groups of FIG. 6.
Figure 11:
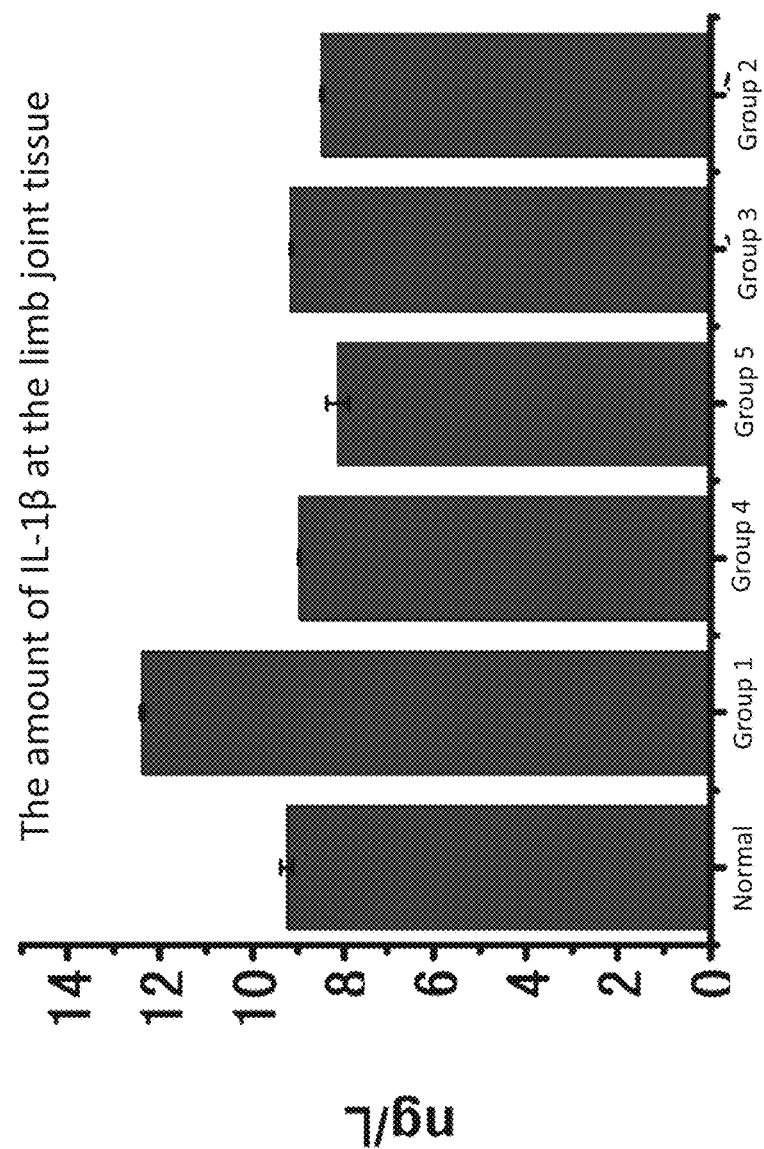
FIG. 11 graphically shows the amount of inflammatory cytokine IL-1β factor at the limb joint area of the different experiment groups of FIG. 6.
Figure 12:
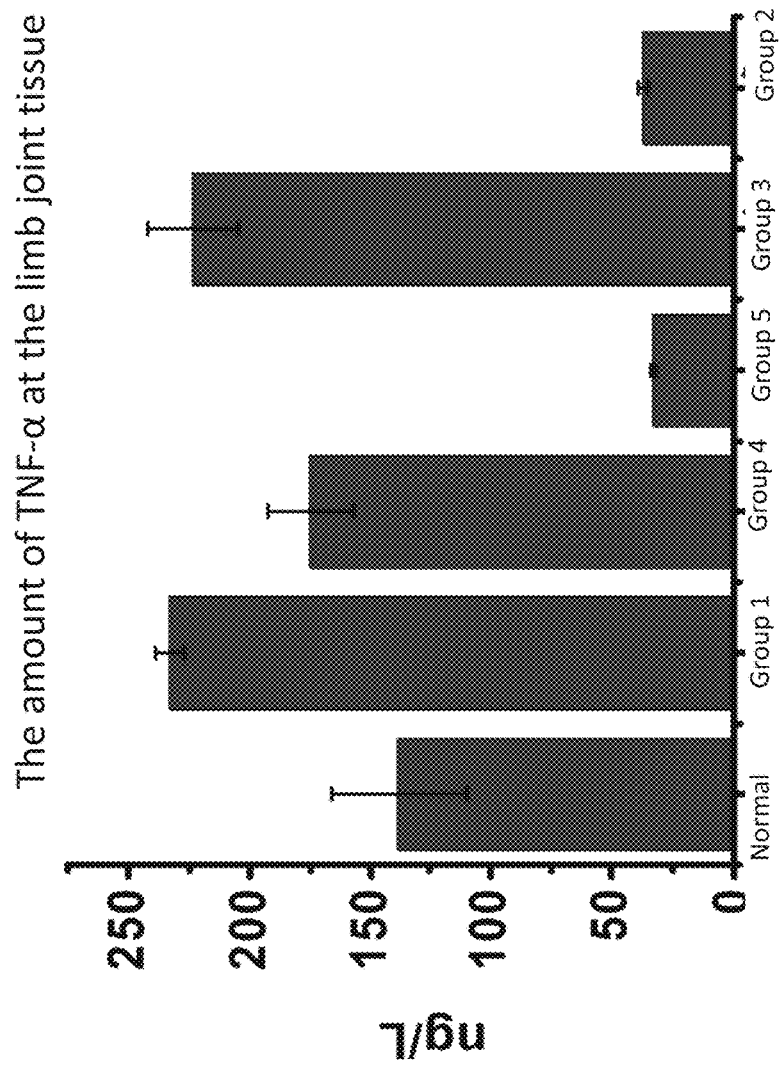
FIG. 12 graphically shows the amount of inflammatory cytokine TNF-α factor at the limb joint area of the different experiment groups in FIG. 6.

In reference to FIGS. 10 and 11, the amount of pro-inflammation cytokine factors IL-6 and IL-1β were measured at the arthritic joints of the variously treated mice groups. Orally (group 4) and intraperitoneally (group 5) administering gold$_{25}$(peptide)$_9$ both reduced these two cytokines to the similar level as that of Dex (group 2), while these two cytokines remained high in auranofin treated mice (group 3).

In reference to FIG. 10, the amount of pro-inflammation cytokine TNF was measured at the arthritic joints of the variously treated mice groups. It shows that intraperitoneally administering of gold$_{25}$(peptide)$_9$ dramatically reduced the TNF generation (group 5) comparing to other treatment methods although Dex (group 2) is the most effective while orally administering of gold$_{25}$(peptide)$_9$ also reduced the amount of TNF (group 4), indicating that the anti-inflammatory and anti-rheumatic role of gold$_{25}$(peptide)$_9$ may be by polarizing the macrophages to the M2 phenotype thus reducing the activation of pro-inflammatory M1 phenotype macrophages which secrete TNF factors. The observed significant differences in effectiveness between orally administering and intraperitoneally administering methods may result from the fact that the amount of gold can be more and directly up-taken through phagocytosis by the macrophage cells peritoneum. This effect is also largely consistent with the prior observation that gold$_{25}$(peptide)$_9$ cluster molecules are capable of induce apoptosis in various cells, and its binding ability of cysteine-rich pro-inflammation cytokines helps with its anti-inflammation effect.

As will be recognized by those skilled in the art, the innovative concepts described in the present application can be modified and varied over a tremendous range of applications, and accordingly the scope of patented subject matter is not limited by any of the specific exemplary teachings given. It is intended to embrace all such alternatives, modifications and variations that fall within the spirit and broad scope of the appended claims.

Additional general background, which helps to show variations and implementations, may be found in the following publications, all of which are hereby incorporated by reference herein for all purposes: N. Ouchi, et al "Adipokines in Inflammation and Metabolic Disease," *Nature Reviews*, 2011, Vol. 11, page 85-95; W. Paska, et al., "Studies on Type II Collagen Induced Arthritis in Mice," *Agents and Actions*, 1986, Vol 18, page 413-420; K. Phadke, et al., "Evaluation of the Effects of Various Anti-Arthritic Drugs on Type II Collagen-Induced Mouse Arthritis Model," *Immunopharmacology*, 1985, Vol 10, page 51-60.

None of the description in the present application should be read as implying that any particular element, step, or function is an essential element which must be included in the claim scope: THE SCOPE OF PATENTED SUBJECT MATTER IS DEFINED ONLY BY THE ALLOWED CLAIMS. Moreover, none of these claims are intended to invoke paragraph six of 35 USC section 112 unless the exact words "means for" are followed by a participle.

The claims as filed are intended to be as comprehensive as possible, and NO subject matter is intentionally relinquished, dedicated, or abandoned.

What is claimed is:

1. A method for attenuating an animal from symptoms of an autoimmune disease, said method comprising the step of:
preparing an therapeutic agent containing a metallic gold cluster molecule agent as active gradient wherein said gold cluster molecule agent has a molecule formula $(gold(0))_n(\text{gold-cluster-capping-molecule})_m$, gold(0) being metallic gold atom as an active gradient and gold-cluster-capping-molecule being a polymer molecule that forms non-covalent metal bond with gold(0), n being the number of gold atoms and m being the number of gold-cluster-capping-molecules, $4000 \geq n \geq 3$ and $110 \geq m \geq 4$, wherein said gold cluster molecule is stabilized by said gold-cluster-capping-molecule and emits fluorescence under excitation UV light; and
administering sufficient amount of said therapeutic agent to said animal.

2. The method of claim 1, wherein said step of administering is through orally method.

3. The method of claim 1, wherein said step of administering is through intraperitoneally method.

4. The method of claim 1, wherein said step of preparing an therapeutic agent further comprises the step of reacting gold (I) or gold (III) salt with gold-cluster-capping-molecule agent at room temperature wherein said gold-cluster-capping-molecule agent is a peptide or protein containing a thiol or arginine or selenol or phosphine or amine side group in a solution or a gold-cluster-capping molecule containing a thiol or arginine or selenol or phosphine or amine side group in a solution, wherein said-gold-cluster-capping molecule is selected from a group consisted of lipids, poly-lysine, poly-arginine, poly-asparagine, poly-aspartic acid sodium salt, poly-aspartic acid sodium salt, poly-glutamate, PEG, PLGA, protein, polysaccharides, nucleic acid, and peptide digestion extracts.

5. The method of claim 4, wherein said peptide or protein has a sequence of SEQ. ID. NO: 1.

6. The method of claim 4, wherein said peptide or protein has a sequence of SEQ. ID. NO: 2.

7. The method of claim 4, wherein said peptide or protein comprises human serum album.

8. The method of claim 1, wherein said autoimmune disease is type II collagen induced arthritis.

9. The method of claim 1, wherein said autoimmune disease is rheumatoid arthritis.

10. A method for attenuating an animal from symptoms of inflammation, said method comprising the step of:
preparing an therapeutic agent containing a metallic gold cluster molecule agent as active gradient wherein said gold cluster molecule agent has a molecule formula $(gold(0))_n(\text{gold-cluster-capping-molecule})_m$, gold(0) being metallic gold atom as an active gradient and fluorescent and gold-cluster-capping-molecule being a polymer molecule that forms non-covalent metal bond with gold(0), n being the number of gold atoms and m being the number of gold-cluster-capping-molecules, $4000 \geq n \geq 3$ and $110 \geq m \geq 4$, wherein said gold cluster molecule is stabilized by said gold-cluster-capping-molecule and emits fluorescence under excitation UV light; and
administering sufficient amount of said therapeutic agent to said animal.

11. The method of claim 10, wherein said step of administering is through orally method.

12. The method of claim 10, wherein said step of administering is through intraperitoneally method.

13. The method of claim 10, wherein said step of preparing an therapeutic agent further comprises the step of reacting gold (I) or gold (III) salt with gold-cluster-capping-molecule agent at room temperature wherein said gold-cluster-capping-molecule agent is a peptide or protein containing a thiol or arginine or selenol or phosphine or amine side group in a solution or a gold-cluster-capping molecule containing a thiol or arginine or selenol or phosphine or amine side group in a solution, wherein said-gold-cluster-capping molecule is selected from a group consisted of lipids, poly-lysine, poly-arginine, poly-asparagine, poly-aspartic acid sodium salt, poly-aspartic acid sodium salt, poly-glutamate, PEG, PLGA, protein, polysaccharides, nucleic acid, and peptide digestion extracts.

14. The method of claim 13, wherein said peptide or protein has a sequence of SEQ. ID. NO: 1.

15. The method of claim 13, wherein said peptide or protein has a sequence of SEQ. ID. NO: 2.

16. The method of claim 13, wherein said peptide or protein comprises human serum album.

\* \* \* \* \*

SEQUENCE LISTING

```
<160> NUMBER OF SEQ ID NOS: 2

<210> SEQ ID NO 1
<211> LENGTH: 13
```

-continued

```
<212> TYPE: PRT
<213> ORGANISM: Artificial sequence
<220> FEATURE:
<223> OTHER INFORMATION: Synthetic construct
<300> PUBLICATION INFORMATION:
<301> AUTHORS: Liu, R
<302> TITLE: The Au Clusters Induce Tumer Cell Apoptosis Via
       Specifically Targeting Thioredoxin Reductase 1 (TrxR1) and
       Suppressing Its Activity
<303> JOURNAL: Chem Commun
<304> VOLUME: 50
<306> PAGES: 10687-10690
<307> DATE: 2014

<400> SEQUENCE: 1

Cys Cys Tyr Gly Gly Pro Lys Lys Lys Arg Lys Pro Gly
1               5                   10

<210> SEQ ID NO 2
<211> LENGTH: 3
<212> TYPE: PRT
<213> ORGANISM: Artificial Sequence
<220> FEATURE:
<223> OTHER INFORMATION: Synthetic construct

<400> SEQUENCE: 2

Glu Cys Gly
1
```